United States Patent [19]

Eckenhoff et al.

[11] Patent Number: 4,539,004
[45] Date of Patent: Sep. 3, 1985

[54] SELF-DRIVEN PUMP ASSEMBLY AND METHOD OF OPERATION

[75] Inventors: James B. Eckenhoff, Los Altos; Virgil A. Place, Half Moon Bay; John R. Peery, Palo Alto, all of Calif.

[73] Assignee: ALZA Corporation, Palo Alto, Calif.

[21] Appl. No.: 602,937

[22] Filed: Apr. 23, 1984

Related U.S. Application Data

[60] Division of Ser. No. 421,597, Sep. 22, 1982, Pat. No. 4,474,575, which is a continuation-in-part of Ser. No. 344,288, Feb. 1, 1982, abandoned.

[51] Int. Cl.³ .............................................. A61M 5/00
[52] U.S. Cl. .................................... 604/131; 604/896
[58] Field of Search ................ 604/56, 131, 132, 151, 604/153, 892, 893, 896

[56] References Cited

U.S. PATENT DOCUMENTS

| | | | |
|---|---|---|---|
| 3,604,417 | 9/1971 | Stolzenberg et al. | 604/131 |
| 3,845,770 | 11/1974 | Theeuwes et al. | 604/893 |
| 3,987,790 | 10/1976 | Eckenhoff et al. | 604/892 |
| 4,340,048 | 7/1982 | Eckenhoff | 604/896 |
| 4,386,929 | 6/1983 | Peery et al. | 604/132 |
| 4,419,096 | 12/1983 | Leeper et al. | 604/132 |
| 4,474,575 | 10/1984 | Eckenhoff et al. | 604/131 |

Primary Examiner—Stephen C. Pellegrino
Assistant Examiner—Michelle N. Lester
Attorney, Agent, or Firm—Steven F. Stone; Edward L. Mandell; Paul L. Sabatine

[57] ABSTRACT

A pump assembly particularly useful as an infusor for parenteral administration of a small amount of a therapeutically active substance for a prolonged period of time at a substantially constant rate comprising a fluid imbibing pump mounted within a receptacle into which actuating fluid may be charged. The active agent is dispensed from the pump after the pump is exposed to the fluid. Means to vary or stop the pump by obdurating all or a portion of the exterior surface of the pump can also be provided. Variation in flow rates can also be obtained by changing the composition of the actuating fluid.

4 Claims, 6 Drawing Figures

SELF-DRIVEN PUMP ASSEMBLY AND METHOD OF OPERATION

RELATED PATENT APPLICATIONS

This application is a division of application Ser. No. 421,597 filed Sept. 22, 1982 now U.S. Pat. No. 4,474,575 which is a continuation in-part of our patent application, Ser. No. 344,288, filed Feb. 1, 1982 for Self-Driven Infusor and Method of Operation now abandoned.

This invention relates to a self-actuated pump designed to dispense a small quantity of a liquid over a prolonged period of time particularly suitable for use in the administration of an active agent. More particularly, this invention relates to a simple compact inexpensive, self-actuated infusor which is designed to deliver a relatively constant, small dosage of an active agent for parenteral delivery over a prolonged period of time.

BACKGROUND OF THE INVENTION

Active agents are commonly administered to a subject parenterally either by injection or infusion. The commonly used distinction between the two is that an injection introduces a dosage of drug in a pulse form, either subcutaneously, intramuscularly, intravenously, or intraarterially, whereas an infusion introduces the active agent in a continuous manner over a prolonged period of time, such as, for example, in the conventional intravenous drip.

It is known to the art that it is generally more desirable to eliminate pulse dosages in which a relatively large amount of the active agent is rapidly deposited for consumption in the body over a prolonged period of time, in favor of the administration over long periods of time of smaller doses. See, for example, Therapeutic Systems, Pattern Specific Drug Delivery, Concept and Development, Klaus Heilman, George Thieme Publishers, Stuttgart, 1978.

Until recently the only manner by which certain active agents could be delivered in this fashion was through intravenous administration which required that a subject be connected to an intravenous drip apparatus. This required immobilization and sometimes hospitalization of the subject. Recently various devices have been developed of which U.S. Pat. No. 3,895,631 Buckles, et al., July 22, 1975, Liquid Infusion Unit, is representative, which permit the ambulatory administration of intravenous medications. Thus a subject is now freed to lead a relatively normal life while the liquid infusion unit is worn by the patient and delivers a relatively constant amount of active agent over prolonged periods of time. The devices have been quite useful; however, this particular type of device which is powered by an elastomeric bladder, has been designed to dispense relatively large amounts of fluid (in the order of 40–60 milliliters) and is not particularly adaptable to the prolonged administration of small amounts of active agents, especially highly potent or expensive drugs, on the order of less than 10 milliliters. An osmotically activated infusor device for smaller quantities is disclosed in the copending patent application of Benjamin J. Eckenhoff, Ser. No. 246,595 filed Mar. 28, 1981 for Self Driven Hypodermic Injection.

There currently exist devices, which are actuated upon the exposure to a fluid environment, such as the ALZET® miniosmotic pumps and OROS® elementary osmotic pumps available from ALZA Corporation, 950 Page Mill Road, Palo Alto, Calif. 94304 which are designed to release small amounts of materials over prolonged periods of time. For example, ALZET miniosmotic pumps are available which will release $200\mu$ liters of fluid at the rate of $0.5\mu$ liters per hour for 2 weeks or $1\mu$ liter per hour for one week. Others have been produced which release 2 ml of fluid over the same time periods. Such devices are compact and have overall dimensions as small as 3 centimeters in length and 0.7 centimeters in diameter. Similar devices actuated upon exposure to a fluid environment are disclosed in U.S. Pat. Nos. 3,995,631, 3,845,770, 3,916,899, 3,987,790, 3,760,984, 3,760,804, 4,203,440, 4,016,880, 4,111,202, 4,111,203, 4,203,442, and 4,210,139 for example which are incorporated herein by reference. Although there are differences in structure and details of operations, the term "fluid imbibing pump" as used herein encompasses all such devices and is intended to include any dispensing device which is caused to expel its contents over an extended period of time upon immersion in a fluid. In operation, these devices are implanted within the body of the subject or are ingested or otherwise introduced into the G.I. tract and are actuated by the imbibition of liquid, i.e., water, from the body inwardly through the permeable or semipermeable membrane creating a pressure differential sufficient to expel the fluid contents of the pump through an outlet orifice at a constant rate throughout the operation of the device. Such devices are particularly useful in experimental and therapeutic administration of active agents to humans and animals, but they are dependent on the body fluids for activation and have not been applied externally. In addition, the flow rate of these devices is predetermined and variations including stopping and restarting after start up are not easily achieved. According to this invention, a lightweight, compact, inexpensive, self-contained externally mounted pump which is capable of dispensing a relatively small amount of liquid over a prolonged period of time is provided. In addition, in certain embodiments of this invention, means are provided by which this basal or tonic dispensing rate can be varied.

It is accordingly an object of this invention to provide a self-contained, externally mounted pump particularly useful for introducing small amounts of an active agent into a subject over a prolonged period of time.

It is another object of this invention to provide a pump in which the flow rate may be varied, including being stopped and restarted.

It is another object of this invention to provide a self-powered infusor which is capable of operating with existing fluid imbibing pumps.

These and other objects of the invention will be readily apparent from the following description with reference to the accompanying drawings wherein.

DESCRIPTION OF THE INVENTION

In its broadest aspect, the objects described above are obtained by a pump assembly which consists of a fluid imbibing pump of the types described in the aforementioned prior art mounted in a suitable liquid impermeable housing, which housing is provided with means by which the housing may be charged with the fluid by which the pump is actuated and means for discharging the active agent from the pump assembly. If the fluid imbibing pump is initially empty, means for charging the fluid imbibing pump with active agent are also provided.

The rate at which the pump assembly delivers can be varied from the maximum flow rate for which the fluid imbibing pump is designed by providing means for varying the external area of the fluid imbibing pump that is exposed to the actuating media. It should be noted that while the prior art fluid imbibing pumps are actuated by water because of their being exposed to body fluid, according to this invention, the actuating medium need not be water. The pump assembly can contain any fluid (non-destructive of the components, of course) and the fluid imbibing pump component is not dependent for actuation upon a liquid which is available within the body. Thus while the pumps of the prior art have a nominal pumping rate normally established with respect to the rate at which body fluids are imbibed into the pump, the infusor of this invention can be made to operate at pumping rates higher or lower than nominal by using fluids whose imbibition rate into the pump is either higher or lower than body fluid. Thus although the specific embodiments described hereinafter relate to aqueous actuation; it should be recognized that these are merely preferred embodiments and are not limiting of the invention.

Figure 1:
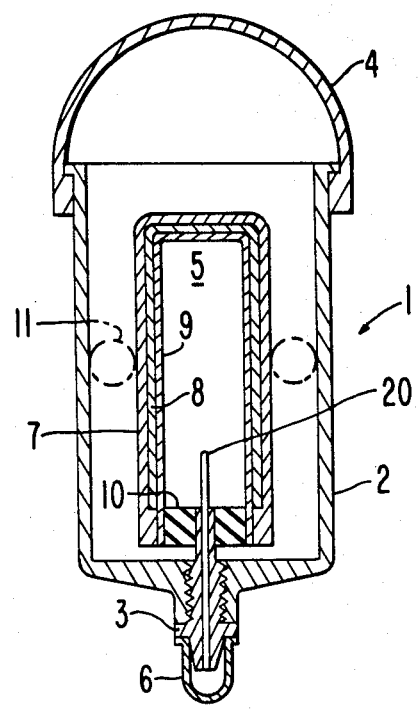
FIG. 1 is a schematic cross-sectional view of an embodiment of this invention.

Referring now to FIG. 1, a basic embodiment of the invention is shown. The pump assembly, numbered generally as 1, according to this invention, comprises a liquid impermeable housing 2; one end being adapted to receive fitting 3 and the other end adapted to engage closure means 4. A fluid imbibing pump shown generally as 5 is mounted within housing 2 on outlet tube 20 which extends from fitting 3 in fluid-sealing relationship with plug 10. A cap 6 is provided over the end of fitting 3 to provide a unit when used for medical purposes which when used for medical purposes may be sterilized by radiation sterilization, for example, and shipped as a unit to be charged with sterile materials, as is hereinafter described, for operation. Pump assembly 1 must be provided with means for introducing the actuating fluid into housing 2 and around pump 5 and preferably, means should also be provided to relieve any vacuum that is created within container 2 during operation as the actuating fluid which is charged into container 2 is imbibed into pump 5 causing a reduction of the volume of fluid within container 2. In the embodiment shown in FIG. 1, both of these functions are performed by cover 4 which in this embodiment is a flexible bulb formed from a self-sealing flexible rubber material which may be removed and replaced after filling with actuating fluid or through which a hypodermic needle may be pushed for introduction of the actuating fluid. As the fluid imbibes into pump 5, the cover 4 would collapse inwardly to eliminate any back pressure on pump 5. The volume of the collapse capability of bulb cover 4 is preferably at least equal to volume of the fluid which will be imbibed into pump 5 during its operation. The actuating fluid is preferably in the form of a low viscosity liquid however it is contemplated that higher viscosity liquids or gels or a fluid absorbed onto a fibrous wick or porous mat could be used in certain embodiments as the source of actuating fluid for the fluid imbibing pump.

The specific structure of pump 5 does not in and of itself form a part of this invention and it is contemplated that any pump structure which functions by the controlled imbibition of a fluid from an external source to generate a relatively constant internal pressure on a fluid to be dispensed can be used. Preferred embodiments utilize pumps such as disclosed and claimed in U.S. Pat. Nos. 3,987,790 or 3,845,770 for example since such devices are inexpensive and available as the ALZET® miniosmotic pump from ALZA Corporation, 950 Page Mill Road, Palo Alto, Calif. or OROS® elementary osmotic pump. An ALZET miniosmotic pump comprises a rigid semi-permeable membrane 7 which is preferably formed of cellulose acetate, surrounding an osmotically effective solute 8, preferably salt and an impermeable flexible rubber bag 9 preferably formed from styrene-butadiene copolymer. A plug 10 formed of the same material as bag 9 is provided with a central port which is friction fitted around a blunted standard hypodermic needle which is carried on the end of fitting 3. The gauge of the needle is selected to provide the proper orifice diameter and acts as the flow conduit for the pump.

In order to operate device of FIG. 1, it would be inverted from the position shown and the drug to be dispensed charged into pump 5 by means of a smaller gauge hypodermic needle inserted within the port in fitting 3, after removal of protective cap 6. In filling pump 5, the bag 9 is filled until drops of fluid appear at the end of fitting 3. This would eliminate any air from the interior of the pump. The thus charged device when used as a medical infusor, depending upon the drug and its stability and any interaction with the material from which flexible bag 9 is formed, may then be stored for varying periods of time, preferably under refrigeration, until it is needed for use. At that time an actuating fluid such as water would be introduced into housing 2 by means of a hypodermic needle, pushed through flexible cover 4. The end of fitting 3 would then be connected to a suitable catheter leading to a hypodermic needle which would be inserted at the infusion site after the pump has been actuating for sufficient time to free the line from air as evidenced by emission of a substantially constant flow of liquid from the needle. Alternately the pump assembly 1 could be used to deliver fluid to a remote site such as an IV bag or a Y fitting in an IV line to administer the contents of the fluid imbibing pump 5 in conjunction with other therapeutic or beneficial agents for example.

The pump assembly 1 can be affixed to the body at some convenient location by means of adhesive tape, Velcro® straps or other suitable attachment means which are not shown in the drawing for clarity. In view of its small size the infusor can be mounted in any convenient location preferably as close as possible to the infusion or delivery site and at least approximately the same height to minimize gravitational back pressure. In operation, when fluid imbibing pump 5 has dispensed its contents it may merely be disconnected at fitting 3 from the catheter leading to the site of infusion and replaced by another charged unit to permit continued dispensing of the active agent. As noted above, cover 4, by means of its being a flexible self-sealing bulb, serves both to reduce the back pressure and provide the means by which the actuating fluid is introduced into the infusor. It should be noted that other means may be used and resealable septums or vacuum release valves may be utilized instead. However, it should be recognized that if a vacuum release valve is employed, the introduction of air into container 2 could permit sloshing of actuating fluid, thereby varying in an uncontrolled manner the area of the exterior surface of pump 5 exposed to the actuating fluid and this could affect the discharge rate of the pump as will be more fully explained hereafter. In this case a gel form of the actuating fluid or a cylindrical wick having absorbed actuating fluid would be preferable.

By locating fluid imbibing pump 5 within a container which isolates it from ambient conditions, several unique results are obtained. For example, one fluid imbibing pump design, which normally could be expected to produce one pumping rate, can be used to produce various pumping rates by appropriate selection of the fluid in which the pump is immersed. Thus, for example, a pump which is designed to have an output of 1 μl per hour, when bathed in an actuating fluid having the osmotic properties of body fluid, can produce a higher output when immersed in distilled water and a lower output when immersed in more concentrated saline solution. Further, since the pump assembly 1 is mounted externally, rather than implanted in the user, it is also possible to vary the flow rate, including a stop-start function, by withdrawing all or a portion of the actuating fluid from container 2, or by varying the concentration or composition of the actuating fluid or by varying the area of the fluid imbibing pump which is exposed to the actuating fluid or, any combination of the above techniques. For example, an O-ring 11 (shown in phantom lines) could be installed between the interior of container 2 and the exterior of fluid imbibing pump 5 to provide a fluid-tight seal with fluid being introduced only above the O-ring 11. Suitable gradations or other markings correlating the O-ring location to flow rate, could be placed on the outside of receptacle 2 to assit in O-ring placement to produce any desired lessening of the flow rate. Alternatively, a cylindrical wick carrying the actuating fluid could be slipped around the pump 5 and cut to the desired length.

Further, if the amount of actuating fluid to which the fluid imbibing pump is exposed can be made less than the volumetric capacity of the pump, it is possible to provide for the discharge of less than the entire contents of the pump at one particular time. Thus, for example, in the embodiment shown in FIG. 1 (which is not to scale), by appropriate selection of the sizes of the internal diameter of container 2, the volume within cap 4 and the location of O-ring 11 it is possible to define an actuating fluid volume within the container 2 which is less than the total internal volume of pump 5 thereby providing for the dispensing of a dosage less than full capacity of the pump over any one particular time interval.

Figure 2:
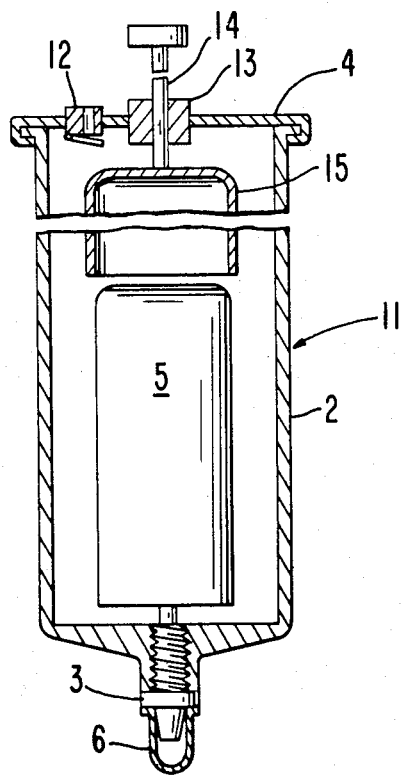
FIG. 2 is a partially cross-sectional view of another embodiment of this invention with means of permitting variation of the flow rate.
Figure 3:
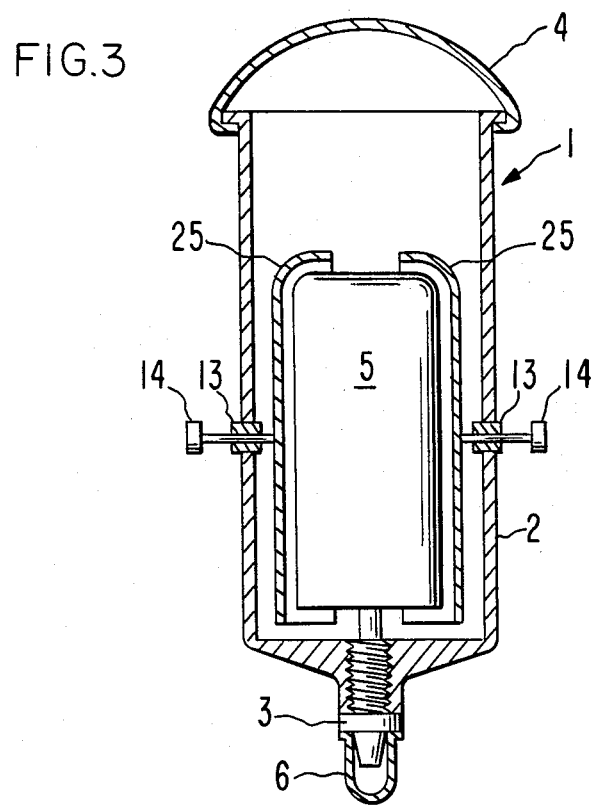
FIG. 3 is a partially cross-sectional view of another flow rate varying embodiment of this invention.

Referring now to FIG. 2, another embodiment of pump assembly 1 according to this invention is shown which is provided with means for varying the flow rate, including a stop-restart function, (like reference numerals refer to like elements in FIG. 1). In this embodiment, container 2 is provided with a rigid cover 14 which is provided with a check valve 12 and a gland 13 through which actuating rod 14 for obdurating member 15 passes in sliding, fluid sealing relationship. Obdurating member 15 is preferably formed from a relatively shape retaining yet flexible element sized internally sightly larger in diameter than the external diameter of pump 5. Obdurating member 15 should obviously be made from a material which is chemically resistant and non-reactive to the actuator fluid used to activate pump 5 and under most circumstances, a rubbery or polymeric material would be suitable. In operation, container 2 would be charged with the actuating liquid through check valve 12 and when obdurating means 15 is maintained above fluid imbibing pump 5, the device will deliver active agent within pump 5 at the designed flowrate. When obdurating member 15 is forced downward over and around pump 5, by pressure on the actuating rod 14, which may be graduated or otherwise marked to indicate the change in flow rate, a portion of the external surface of pump 5 will be shielded from the actuating fluid thereby reducing the rate of discharge. By making member 15 slightly flexible, it is possible to provide a tolerance which permits easy displacement of member 15 around pump 5 and as the pump imbibes the small amount of fluid retained between member 15 and pump 5, a fluid-tight seal will be formed between the two. By pushing obdurating number 15 to its full inward extent, it is possible to substantially completely envelop pump 5 within member 15, thereby causing the pump to cease operation within a very short period of time. The pump 5 can then be reactivated if its contents have not been completely expelled by simply withdrawing obdurating member 15 back to its original position or any intermediate position therebetween. The pump assembly 1 shown in FIG. 2 produces its flow rate control by longitudinal obduration of pump 5; however, it is recognized that this may undesirably increase the length of the overall device. As shown in FIG. 3, a similar effect can be obtained through the use of a plurality of laterally movable obdurating members 25 which are actuated by application of pressure to actuating means 14 extending through glands 13 in the wall of container 2. Also as noted above, the devices of FIGS. 2 or 3 can be shut off by the withdrawal of receptor fluid from container 2 by means of a hypodermic needle, for example.

Figure 4A:
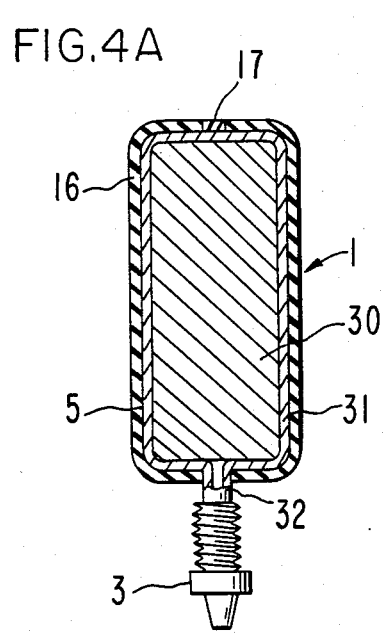
FIGS. 4a and 4b are partially cross-sectional views of another embodiment of this invention.
Figure 4B:
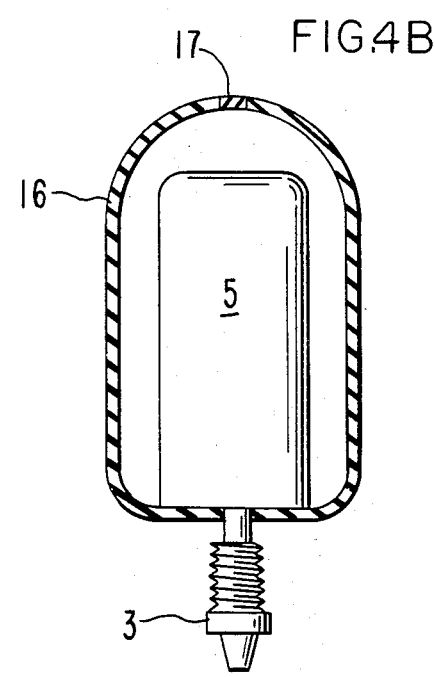

Referring now to FIGS. 4a and b, another embodiment of the invention is shown in which the pump assembly 1 comprises a fluid imbibing pump 5 provided with an impermeable, expandable membrane 16 formed of a rubber material, for example, which if it is not self-sealing, may provide with a sealable septum 17 or check valve through which a precise volume of actuating fluid may be introduced between member 16 and pump 5 to inflate membrane 16 as shown in FIG. 4b. Since the amount of fluid expelled from pump 5 cannot be greater than the volume of fluid imbibed into the pump, by controlling the volume of fluid introduced into membrane 16, a control of the portion of the dose contained within pump 5 that can be dispensed at any one time will be obtained. The pump assembly 1 of FIG. 4 can be used affixed to the body by suitable attaching means, not shown, or mounted within a housing (such as 2 in FIG. 1) for protection, the housing itself being affixed to the body.

Fluid imbibing pump 5 in this embodiment is shown as an OROS elementary osmotic pump such as described in FIG. 1 of U.S. Pat. No. 3,845,770 in which an osmotically active solute 30 is contained within a rigid, semipermeable membrane 31 provided with an outlet 32. This pump does not employ a collapsible or movable element to expel its contents, instead as the solvent passes through the semipermeable membrane, the solute is dissolved and the saturated solution formed is pressurized as a result of the osmotic pressure generated within membrane 31.

While as described above the pump assembly of this invention may be mounted on the body and used to introduce agents into the body by connecting fitting 3 to a needle for penetration of the skin in proximity to the mounting site; the pump assembly can also be used to deliver fluid to a remote location. The pump may be mounted on the body or may be mounted on or connected to other apparatus such as an I.V. set, a feeding tube or a catheter assembly, for example.

Figure 5:
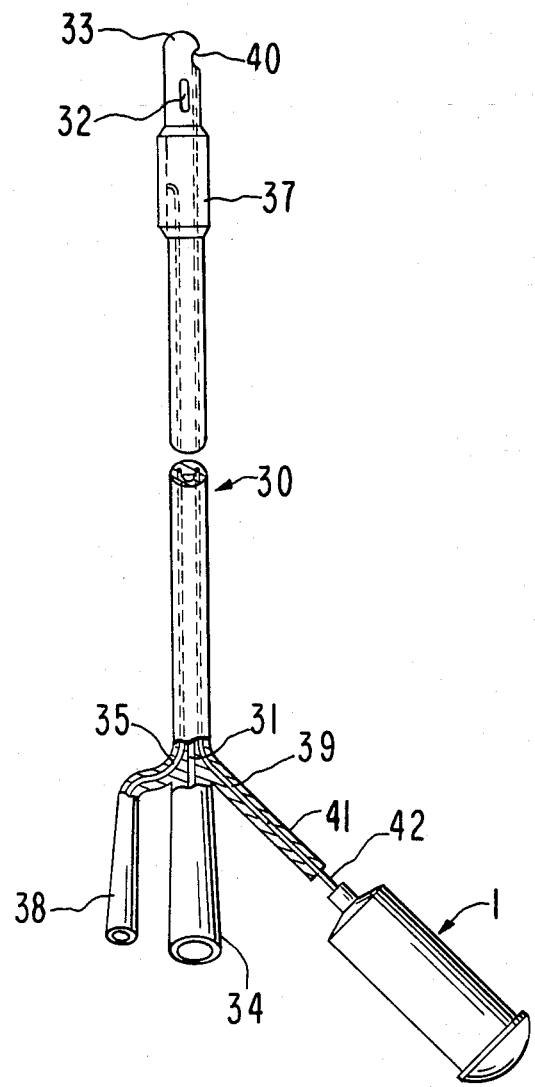
FIG. 5 is a schematic representation of the use of the pump of this invention to deliver an active agent to a remote location.

Referring now to FIG. 5 the pump assembly 1 of this invention is shown in combination with a 3-lumen Foley irrigation and drainage catheter 30, having a draining lumen 31 communicating with eye 32 adjacent the distal tip 33 and terminating proximally in the funnel 34. The inflation lumen 35 communicates with the interior of the balloon 37 and terminates proximally in the inflation funnel 38 which may be closed by a suitable valve, not shown. The third lumen 39 extends from the eye 40, located as close as practicable to the tip 33 of the catheter, to the inlet end 41 in which pump assembly 1 is mounted. A hollow needle 42 is mounted over fitting 3 (FIG. 1) which needle is sized slightly larger than lumen 39 to form a seal with the wall and prevent leakage around needle 42. In operation the pump assembly would be charged with an agent such as an antibiotic and the actuating fluid as described above, and after agent discharge from eye 40 had been verified the catheter 30 inserted and inflated in the usual manner. The pump 1 will deliver a continuous flow of antibiotic to the urinary bladder and also to the urethral wall and can be used to prevent urinary tract infections which currently occur in a significant portion of the catheterized patient population.

EXAMPLE

An ALZET mini-osmotic pump, Model No. 2ML1 is mounted in a rigid container provided with a flexible deflatable dome cover by means of a 26-gauge blunt needle tube on a standard Vacutainer® fitting provided with a rubber end cap. The whole assembly is sterilized (60Co, 2.5 Mrad). Prior to use the pump is filled with a fluid active agent from a prefilled syringe by insertion of a blunt needle into the end of the fitting after removal of the end cap. The pump is filled until the active agent appears at the tip of the fitting at which time the needle is removed and the end cap replaced. Depending on chemical compatibility of the reservoir material with the active agent formulation, the filled pump can be stored under special conditions (refigeration) for upwards of one month.

To use, the housing is charged with sterile actuating liquid using a standard 21 gauge (½ inch) syringe needle and a syringe. The syringe is first prefilled with sterile liquid and is then attached to the 21 gauge syringe needle. The needle is inserted through the rim of the elastomeric bulb and by alternating pushing and pulling on the plunger of the syringe, the air is evacuated from the housing and replaced with liquid. Once filled with liquid, the pump assembly is charged. The pump assembly is then connected to a standard butterfly infusion set at the fitting. After an initial transient start-up period (ending when a steady flow of fluid is emitted from the needle of the infusion set), which can be accomplished on-the-shelf prior to patient hook-up, the pump assembly will deliver its contents at a constant rate. Variation of pumping rate over time is independent of rate and is constant within ±10%. The pump assembly is attached to the subject by a Velcro strap and the infusion needle inserted at the appropriate site under standard sterile insertion techniques.

When the actuating liquid is isotonic saline solution, at an operating temperature of 32° C. the infusor will discharge at a nominal pumping rate of 7.9μ liters per hour for approximately 2 weeks. When the actuating liquid is distilled water the infusor will discharge at a nominal pumping rate of approximately 8.4 μl/hr for approximately 11 days, whereas if exposed to a 10% saline solution, it will discharge at 2.3 μl/hr for approximately 4 weeks. The equation which relates discharge rate for this osmotic pump to operating temperature and osmolality of the surrounding liquid is:

$$Q = Q_o(0.141 e^{0.051T} - 0.007\pi + 0.12)$$

where $Q_o$ is the design discharge rate (l/hr) in isotonic saline at 37° C. and T and $\pi$ are actual temperature (°C.) and osmolality (atm) of imbibing fluid. When the active agent is unmodified crystaline bovine insulin U-500 diluted with isotonic saline to 100 units/ml, 19 units per day for 2 weeks will be delivered at the flow rate obtained with isotonic saline solution which is in the therapeutic range for human class I diabetics.

While this invention has been described with respect to certain embodiments thereof, it should not be construed as being limited thereto. Various modifications may be made by workers skilled in the art without departing from the scope of this invention which is limited only by the following claims, wherein:

We claim:

1. A pump assembly for delivering small amounts of a fluid for a prolonged period of time comprising, in combination:
   (a) fluid impermeable container means provided with outlet means;
   (b) fluid imbibing pump means mounted within said container means the outlet of said pump means being in fluid communicating relationship to the outlet in said container means, the interior of said container means and the exterior of said pump means defining therebetween a fluid receiving volume sufficient, when charged with actuating fluid to actuate said pump; and
   (c) at least a portion of said fluid impermeable container means being formed from a flexible, collapsible, impermeable material which portion has a collapse capacity at least equal to the discharge capacity of said fluid imbibing pump, whereby imbition of fluid contained within the fluid receiving volume during actuation of said pump means will not create a vacuum of said fluid imbibing pump means.

2. The pump assembly of claim 1 wherein said flexible collapsible wall portion is formed from an elastic material expansible from (i) an initial condition in close fitting relationship to the exterior of said fluid imbibing pump; to (ii) an expanded condition having a volumetric capacity at least equal to the volume of fluid to be discharged from said fluid imbibing pump means.

3. The pump assembly of claim 1 wherein at least a portion of said flexible, collapsible, impermeable material is provided with self-sealing means through which actuating fluid may be introduced between said material and said fluid imbibing pump means.

4. The pump assembly of claim 2 wherein at least a portion of said elastic material is provided with self sealing means through which actuating fluid may be introduced between said elastic material and said fluid imbibing pump means.

* * * * *